(12) United States Patent
Chand et al.

(10) Patent No.: US 7,230,119 B2
(45) Date of Patent: Jun. 12, 2007

(54) PROCESS FOR THE PREPARATION OF SUBSTITUTED PYRROLIDINE DERIVATIVES AND INTERMEDIATES

(75) Inventors: Pooran Chand, Birmingham, AL (US); Yahya El-Kattan, Hoover, AL (US); Pravin L. Kotian, Hoover, AL (US)

(73) Assignee: BioCryst Pharmaceuticals, Inc., Birmingham, AL (US)

( * ) Notice: Subject to any disclaimer, the term of this patent is extended or adjusted under 35 U.S.C. 154(b) by 46 days.

(21) Appl. No.: 11/210,691

(22) Filed: Aug. 25, 2005

(65) Prior Publication Data

US 2006/0128789 A1 Jun. 15, 2006

Related U.S. Application Data

(60) Provisional application No. 60/604,042, filed on Aug. 25, 2004.

(51) Int. Cl.
*C07D 207/06* (2006.01)
*C07D 207/08* (2006.01)
*C07D 207/09* (2006.01)

(52) U.S. Cl. ...................................... 548/535; 548/556

(58) Field of Classification Search ................ 548/535, 548/556

See application file for complete search history.

(56) References Cited

OTHER PUBLICATIONS

Karlsson, et al., Tetrahedron; Asymmetry 12 (2001) 1977-1982.*
Tetrahedron Letters 41 (2000) 2949-2951.*
Tetrahedron Asymmetry 10 (1999) 2605-2616.*

* cited by examiner

*Primary Examiner*—Kamal A. Saeed
*Assistant Examiner*—Nyeemah Grazier
(74) *Attorney, Agent, or Firm*—Connolly, Bove, Lodge & Hutz, LLP

(57) ABSTRACT

Two syntheses are provided; one for the preparation of (3R,4R)-4-(hydroxymethyl)pyrrolidin-3-ol, and other for the preparation of (3S,4R)-4-(hydroxymethyl)pyrrolidin-3-ol. (3R,4R)-4-(hydroxymethyl)pyrrolidin-3-ol is prepared using the achiral ylide prepared from benzylamine instead of phenethylamine (Scheme 3) which provides a crystalline intermediate. The synthesis of (3S,4R)-4-(hydroxymethyl) pyrrolidin-3-ol is achieved from (S)-diethylmalate as described in Scheme 4. A process for preparing camphor sultam is also provided.

10 Claims, No Drawings

PROCESS FOR THE PREPARATION OF SUBSTITUTED PYRROLIDINE DERIVATIVES AND INTERMEDIATES

CROSS REFERENCE TO RELATED APPLICATIONS

The present application claims priority from U.S. Provisional Application Ser. No. 60/604,042, filed Aug. 25, 2004, and entitled Preparation of Hydroxymethyl Substituted Pyrrolidine Derivatives, the entire disclosure of which is incorporated herein by reference.

TECHNICAL FIELD

The present disclosure is concerned with a procedure for producing substituted pyrrolidine derivatives. This disclosure provides an economical route to produce substituted pyrrolidines. This procedure also makes possible large scale production of the pyrrolidine derivatives. The present disclosure also relates to a process for preparing camphor sultam, an intermediate that can be used in the present disclosure. The present disclosure also relates to certain intermediates used in preparing the substituted pyrrolidine derivatives.

BACKGROUND INFORMATION

Racemic and non-racemic 4-(hydroxymethyl)pyrrolidin-3-ols have been prepared and found to have an inhibitory effect on certain enzymes and on glial GABA uptake. These pyrrolidines have also been used as building blocks for the synthesis of some compounds having antibacterial activity and also for some nucleosides analogues. Recently, (3R,4R)-4-(hydroxymethyl)-pyrrolidin-3-ol was used for the synthesis of a highly potent purine nucleoside phosphorylase (PNP) inhibitor.

The first synthesis of 3-hydroxy-4-hydroxymethylpyrrolidine was reported starting from N-benzylglycinate and ethyl acrylate and was obtained as a mixture of cis/trans isomers. The trans-racemic compound was prepared starting from fumaric acid methyl ester.

The first synthesis of the pure enantiomer (3R,4R)-4-(hydroxymethyl)pyrrolidin-3-ol was reported from glucose and xylose (Schemes 1 and 2) in very low yields requiring several steps and is not practical for synthesis on a kilogram scale.

Karlsson and Hogberg reported the preparation of this compound via asymmetric 1,3-dipolar cycloaddition using camphor sultam as a chiral auxiliary. In this synthesis, the chiral ylide used was generated from phenethylamine and the intermediates obtained were oils requiring flash chromatography for the separation of isomers.

These reported methods are considered unsuitable for various reasons. To produce kilogram quantities of these products, a practical synthesis was needed using a suitable procedure.

BRIEF SUMMARY OF THE DISCLOSURE

Two different syntheses were developed, one for the preparation of (3R,4R)-4-(hydroxymethyl)pyrrolidin-3-ol, and other for the preparation of (3S,4R)-4-(hydroxymethyl)pyrrolidin-3-ol. The synthesis of (3R,4R)-4-(hydroxymethyl)pyrrolidin-3-ol was achieved through reinvestigation of the 1,3-dipolar cycloaddition using the achiral ylide prepared from benzylamine instead of phenethylamine (Scheme 3) which provides a crystalline intermediate. The synthesis of (3S,4R)-4-(hydroxymethyl)pyrrolidin-3-ol was achieved from (S)-diethylmalate as described in Scheme 4. These methods provide a significant improvement over prior art methods and are easy to manipulate on a large scale and give higher overall yields of the desired compounds.

The present disclosure also relates to a process for preparing camphor sultam, an intermediate in the method for preparing (3R,4R)-4-(hydroxymethyl)pyrrolidin-3-ol.

Another aspect of the present disclosure relates to certain of the intermediates employed in preparing the substituted pyrrolidine derivatives and namely, (2S,3R)-2-(Benzyloxymethoxy)-3-(benzyloxymethyl)butane-1,4-diol; (2S,3S)-2-(Benzyloxymethoxy)-3-(benzyloxymethyl)butane-1,4-diyl dimethanesulfonate; and (3S,4R)-1-Benzyl-3-(benzyloxymethoxy)-4-(benzyloxymethyl)pyrrolidine.

BEST AND VARIOUS MODES FOR CARRYING OUT DISCLOSURE

The present disclosure relates to a process for preparing a compound of formula (I)

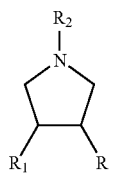

wherein
R is selected from the group consisting of H, $OR_2$, $N_3$, $NHR_2$ and F;
$R_1$ is selected from the group consisting of $CH_3$, $CH_2OR_2$, $CH_2N_3$, $CH_2NHR_2$, $CH_2F$, CHO, $CH=NR_2$, $CO_2H$, $CO_2$ alkyl, $CONHR_2$, $CH_2CH_2OR_2$, $CH=CHCO_2R_3$, $CH_2CH_2CO_2R_3$ and $CH_2CH_2CH_2OR_2$;
$R_2$ is selected from the group consisting of H, $R_3$, $CH_2R_3$, $C(O)R_3$ and $C(O)OR_3$; and
$R_3$ is selected from the group consisting of alkyl and aryl; and pharmaceutically acceptable salts thereof.

The expression "alkyl" refers to unsubstituted alkyl groups of 1 to 4 carbon atoms. Examples of suitable alkyl groups include methyl, ethyl and propyl. The term "aryl" refers to monocyclic or bicyclic aromatic hydrocarbon groups having 5 to 8 atoms in the ring portion, such as phenyl. The monocyclic aryl groups are typically are 5 to 7 membered rings, and the bicyclic aryl groups are typically 7 to 8 membered rings. The aryl group can optionally contain 1, 2 or 3 heteroatoms selected from nitrogen atoms, oxygen atoms and sulfur atoms, where the nitrogen and sulfur heteroatoms are more typical. Examples of aryl groups containing heteroatoms are thiophenyl, furanyl, pyrrolyl, pyrazolyl, pyridinyl, pyrimidinyl pyridazinyl and pyranyl.

Pharmaceutically acceptable salts of the compounds of the present disclosure include those derived from pharmaceutically acceptable inorganic or organic acids. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include alkali such as sodium and ammonia.

The process for the preparation of compound (Ia) where R and $R_1$ are trans to each other in formula (I) comprises the following steps:

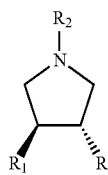

(Ia)

i) reacting camphor sulfonic acid with thionyl chloride; then contacting the resultant camphor sulfonyl chloride with ammonia to generate camphor sulfonamide; eliminating water from the amide under acidic conditions, with pH of 4 to 1 to produce an imine; and hydrogenating the resultant imine with hydrogen in the presence of a suitable catalyst to produce camphor sultam (3-1) under reaction conditions, such as at a hydrogen pressure of about 30 to about 200 psi, more typically about 40 to about 120 psi; in the presence of a catalyst such as Raney Ni, Pd/C, Pd(OH)$_2$, more particularly Raney Ni; and at a temperature of about 20° C. to about 60° C., more typically room temperature.

ii) then reacting an acrylic acid chloride such as (E)-3-benzyloxyacrylic acid chloride (3-2) with camphor sultam (3-1) and a base, such as methyl magnesium bromide at a suitable temperature, and appropriate equivalents of reagents to yield the addition product (E)-3-benzyloxypropenoyl-(2'S)-borane-10,2-sultam (3-3) at a temperature of about −30° C. to about −40° C. The benzyloxy group of the above exemplified acid chloride is used for introducing a hydroxyl in the molecule, when desired. Exemplary relative amounts are camphor sultam: methyl magnesium bromide: acid chloride of 1.0:1.1:0.8.

iii) contacting chloromethyltrimethylsilane with benzylamine to generate N-(trimethylsilylmethyl)benzylamine and then reacting N-(trimethylsilylmethyl)benzylamine with formaldehyde and methanol to produce N-(benzyl)-N-(methoxymethyl)-N-(trimethylsilylmethyl)amine (3-4), which can typically be carried out at a temperature of about 10° C. to about 15° C. and typically completed within about 3 hours.

iv) reacting compound 3-3 with compound 3-4 in the presence of a acid catalyst, such as trifluoroacetic acid to produce pyrrolidine derivatives 3-5 and 3-6 as a mixture of isomers and isolating the desired isomer 3-5 by crystallizations. This step can typically be carried out using about 1.0 equivalent of 3-3, about 2.0 equivalents of 3-4 and trifluoroacetic acid in a catalytic amount such as about 0.05 equivalent at about room temperature. The crystallization at room temperature can be achieved using ethyl acetate-hexane.

v) reducing compound 3-5 with a reducing agent, such as lithium aluminum hydride, and isolating the pyrrolidine derivative 3-7. This step can typically be carried out using about 1.0 equivalent of 3-5 and about 3.0 equivalents of the reducing agent.

vi) deprotecting compound 3-7 through hydrogenation in the presence of a catalyst such as 10% Pd/C in an amount of about 10 to 100% by weight to produce the desired compound of formula (Ia). This step can typically be carried out at about room temperature and pressure of about 60 to 500 psi.

To further facilitate an understanding of the present disclosure, a process for the preparation of compound (Ia), where R═OH, R$_1$═CH$_2$OH and R$_2$═H and R and R$_1$ are trans to each other in formula (I) comprises the following steps as given in Scheme 3 is shown below:

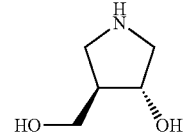

(Ia)

i) reacting camphor sulfonic acid with thionyl chloride; further contacting the resultant camphor sulfonyl chloride with ammonia to generate camphor sulfonamide; eliminating water from the amide under acidic conditions to produce an imine; and hydrogenating the resultant imine with hydrogen in the presence of a suitable catalyst to produce camphor sultam (3-1) under appropriate conditions for reactions to occur such as those discussed above;

ii) further reacting (E)-3-benzyloxyacrylic acid chloride (3-2) with camphor sultam (3-1) and a base, such as methyl magnesium bromide at a suitable temperature as discussed above, and appropriate equivalents of reagents to yield the addition product (E)-3-benzyloxypropenoyl-(2'S)-borane-10,2-sultam (3-3);

iii) contacting chloromethyltrimethylsilane with benzylamine to generate trimethylsilylmethyl)benzylamine and further reacting N-(trimethylsilylmethyl)benzylamine with formaldehyde and methanol to produce N-(benzyl)-N-(methoxymethyl)-N-(trimethylsilylmethyl)amine (3-4) under appropriate conditions for reactions to occur such as those discussed above;

iv) reacting compound 3-3 with compound 3-4 in the presence of a acid catalyst, such as trifluoroacetic acid to produce pyrrolidine derivatives 3-5 and 3-6 as a mixture of isomers and isolating the desired isomer 3-5 by crystallizations under appropriate conditions for reactions to occur such as those discussed above;

v) reducing compound 3-5 with a reducing agent, such as lithium aluminum hydride, and isolating the pyrrolidine derivative 3-7 under appropriate conditions for reactions to occur such as those discussed above;

vi) deprotecting compound 3-7 through hydrogenation in the presence of a catalyst such as Pd/C to produce the desired compound of formula (Ia).

The process for the preparation of compound Ib, where R and R$_1$ are cis to each other in formula (I) comprises of the following the steps:

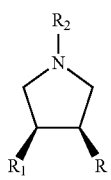

Ib i) alkylating (S)-diethylmalate (4-1) with benzyl chloromethyl ether in the presence of a base such as, LDA (lithium diisopropylamide) to produce 4-2 and isolating the compound. This step can typically be carried out using about 2.1 equivalents of LDA, about 1.0 equivalent of 4-2, and about 2.0 equivalents of benzyl chloromethyl ether at a temperature of about −78° C.

ii) reducing the ester groups of 4-2 with LiAlH$_4$ to generate alcohol 4-3. This step can typically be carried out at a temperature of about 0 to 80° C. with about 2.0 equivalents of LiAlH$_4$ and about 1.0 equivalent of 4-2.

iii) reacting alcohol 4-3 with methanesulfonyl chloride in the presence of a base, such as pyridine to produce dimesylated compound 4-4. This step can be carried out at a temperature of about 0 to 50° C. with about 3.0 equivalents of methanesulfonyl chloride and about 1.0 equivalent of 4-3.

iv) cyclizing dimesyl compound 4-4 with benzylamine to yield pyrrolidine derivative 4-5. This step can typically be carried out at a temperature of about 60° C. in the presence of a large excess of benzylamine which also acts as a solvent in this step.

v) deprotecting compound 4-5 through hydrogenation in the presence of about 10 to 100% by weight of a catalyst such as, 10% Pd/C and acid, such as HCl to produce the desired compound of formula (Ib). This step can be carried out at a temperature of about 0° C. to about room temperature and at a pressure of 60 to 500 psi.

To further facilitate an understanding of the present disclosure, a process for the preparation of compound Ib, where R=OH, $R_1$=$CH_2OH$ and $R_2$=H and R and $R_1$ are cis to each other in formula (I) comprises of the following steps as given in Scheme 4 is shown below:

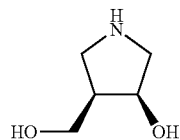

Ib i) alkylating (S)-diethylmalate (4-1) with benzyl chloromethyl ether in the presence of a base such as, LDA (lithium diisopropylamide) to produce 4-2 and isolating the compound under appropriate conditions for reactions to occur such as those discussed above;

ii) reducing the ester groups of 4-2 with $LiAlH_4$ to generate alcohol 4-3 under appropriate conditions for reactions to occur such as those discussed above;

iii) reacting alcohol 4-3 with methanesulfonyl chloride in the presence of a base, such as pyridine to produce dimesylated compound 4-4 under appropriate conditions for reactions to occur such as those discussed above;

iv) cyclizing dimesyl compound 4-4 with benzylamine to yield pyrrolidine derivative 4-5 under appropriate conditions for reactions to occur such as those discussed above;

v) deprotecting compound 4-5 through hydrogenation in the presence of a catalyst, such as Pd/C, to produce the desired compound of formula (Ib).

Discussions of the above processes can also be found in Kotian et al, An Efficient Stereoselective Synthesis of (3S, 4R)-4-(hydroxymethyl)pyrrolidin-3-ol from (S)-Diethylmalate, Tetrahedron Letters 46 (2005) 3327–3330, Apr. 2, 2005; and Kotian et al, A Practical Large-Scale Synthesis of (3R,4R)-4-(hydroxymethyl)pyrrolidin-3-ol with Asymmetric 1,3-Dipolar Cycloaddiiton, Organic Process Research and Development 2005, 9, 193–197; disclosures of which are incorporated herein by reference.

Scheme 1.

D—Xylose
(1-1)

1. $Me_2CO$, $H_2SO_4$
2. TBDMSCl, Im, DMF

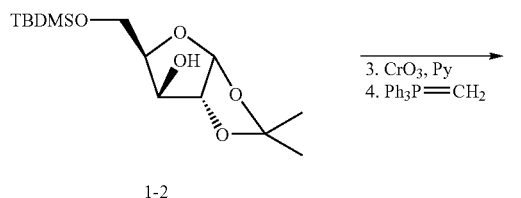

1-2

3. $CrO_3$, Py
4. $Ph_3P$=$CH_2$

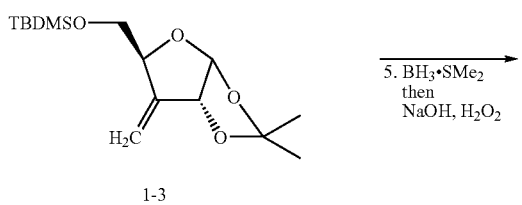

1-3

5. $BH_3 \cdot SMe_2$ then NaOH, $H_2O_2$ 1-4

6. MsCl, Py
7. $NaN_3$

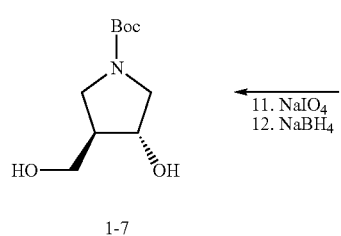 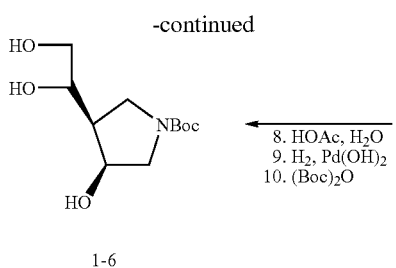 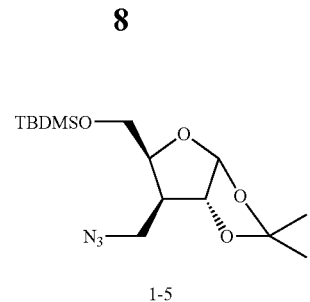

1-7      1-6      1-5

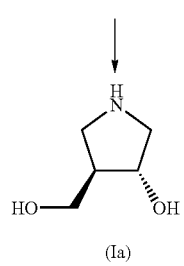

(Ia)

Scheme 2.

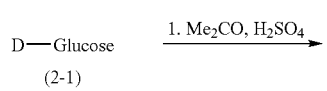

D—Glucose $\xrightarrow{\text{1. Me}_2\text{CO, H}_2\text{SO}_4}$ (2-1)

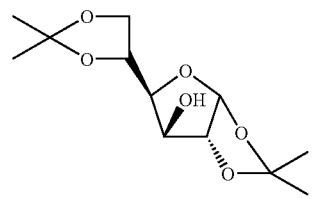

2-2

$\xrightarrow{\text{2. PDC, Ac}_2\text{O, CH}_2\text{Cl}_2}$

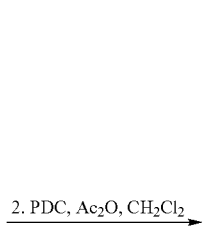     -continued     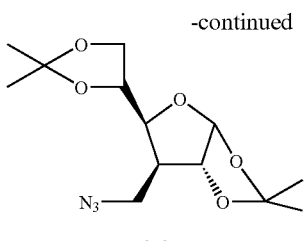

$\xrightarrow{\begin{array}{c}\text{7. H}^+\\ \text{8. H}_2\text{, Pd/C}\\ \text{9. Boc}_2\text{O}\end{array}}$ 2-6

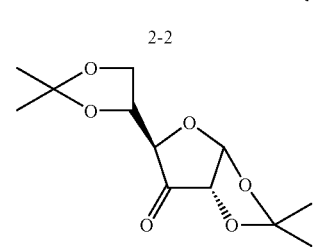

2-3

$\xrightarrow{\text{3. Ph}_3\text{P}=\text{CH}_2\text{, THF}}$

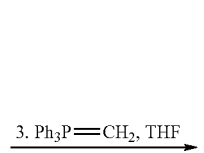    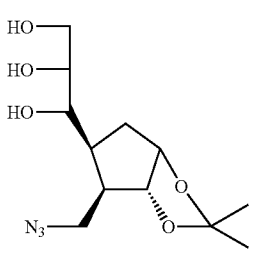

2-7

$\xrightarrow{\begin{array}{c}\text{10. NaIO}_4\text{, EtOH, H}_2\text{O}\\ \text{11. NaBH}_4\text{, EtOH, H}_2\text{O}\end{array}}$

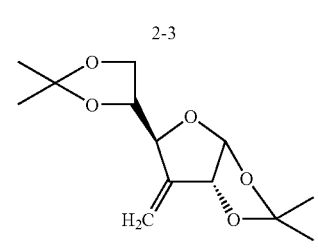

2-4

$\xrightarrow{\begin{array}{c}\text{4. BH}_3\cdot\text{SMe}_2\\ \text{then NaOH, H}_2\text{O}_2,\\ \text{THF}\end{array}}$

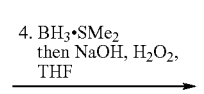     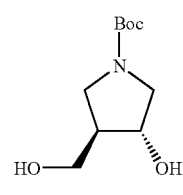

2-8

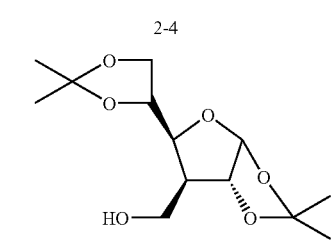

2-5

$\xrightarrow{\begin{array}{c}\text{5. MsCl, }^i\text{PrNEt}_2\\ \text{6. NaN}_3\text{, DMF}\end{array}}$

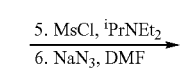     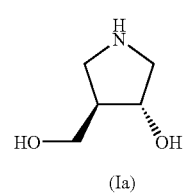

(Ia)

Scheme 3.
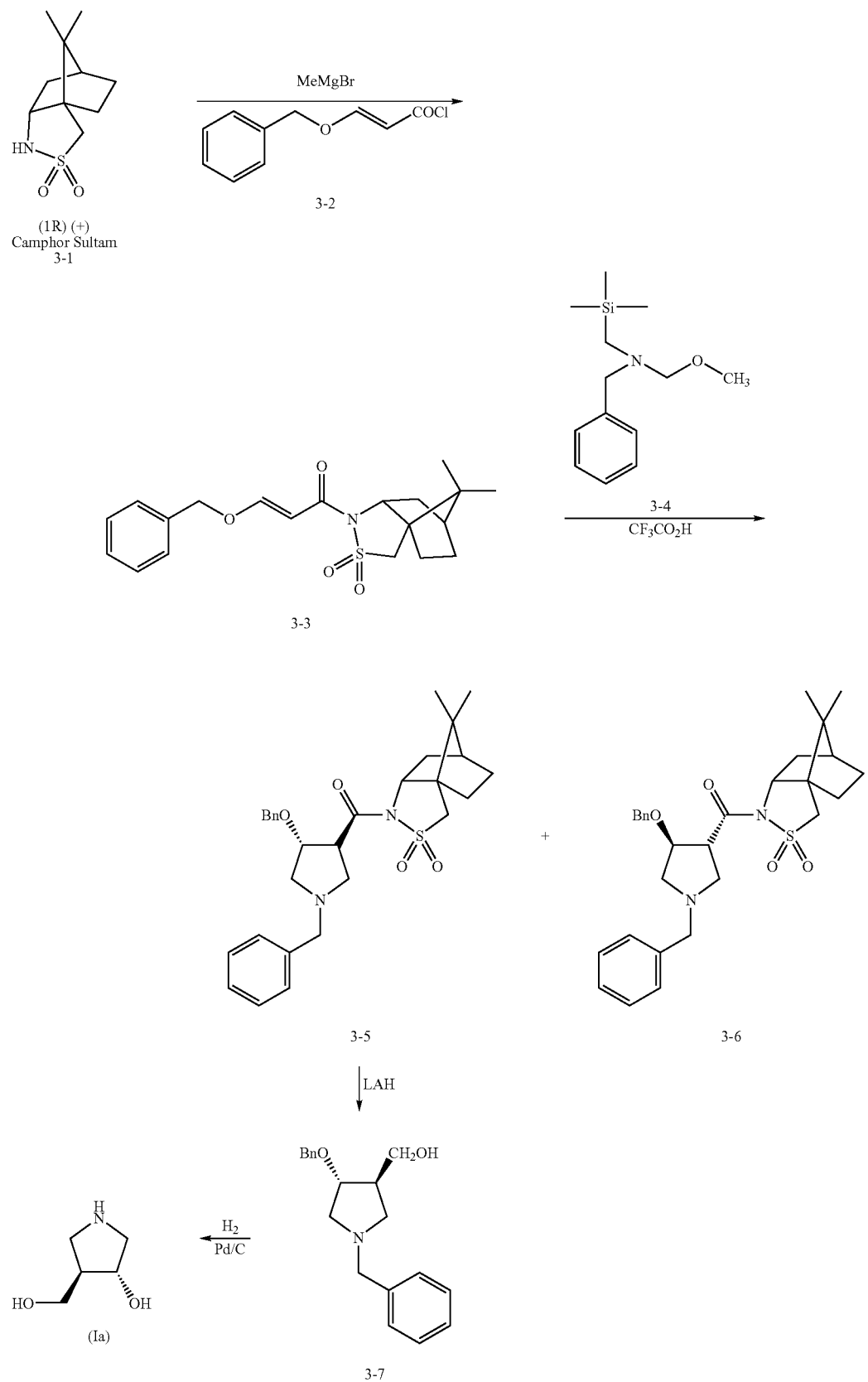

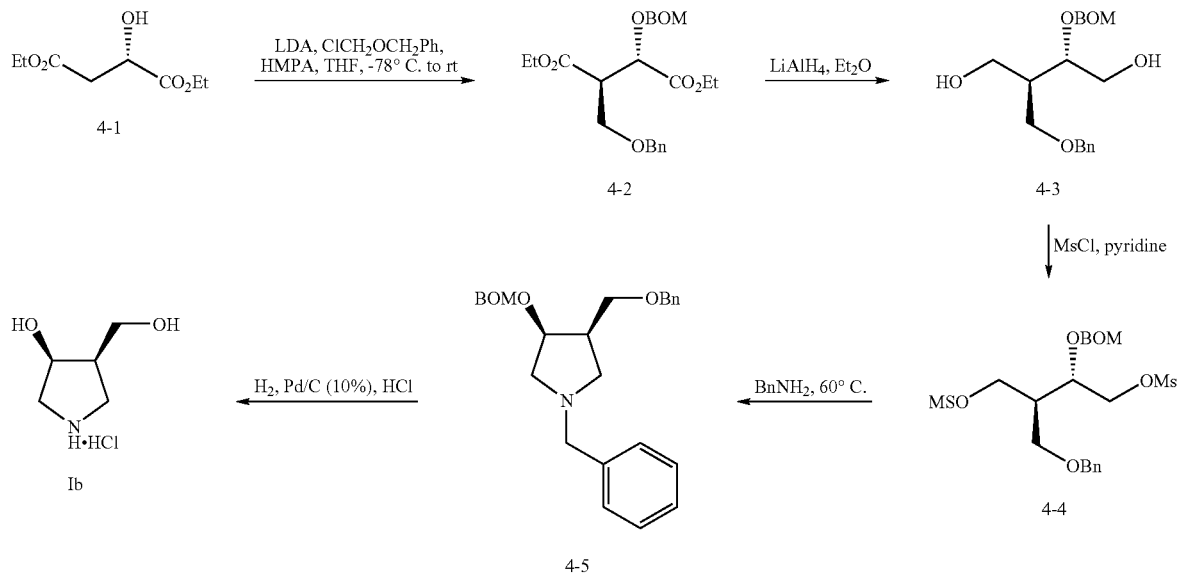

Scheme 4.

The following examples are given below to further illustrate the present disclosure:

EXAMPLE 1

(1R)-(+)-2,10-Camphor Sultam (Scheme 3, 3-1)

To a solution of (−) camphor sulfonic acid (1.45 kg, 6.25 mol) in chloroform (7 L) under reflux condition is added thionyl chloride (0.896 kg, 7.5 mol) over a period of 1 h. The reaction mixture is refluxed for 16 h and then cooled to 4° C. using an ice bath. This cooled reaction mixture is added slowly to conc. NH$_4$OH (15 L) while maintaining the temperature below 15° C. during the addition. After addition, the mixture is stirred for 4 h at room temperature. The organic layer is separated and the aqueous layer is extracted with chloroform (2×2 L). The combined organic extracts are washed with brine (4 L) and dried over MgSO$_4$. After filtration, the filtrate is concentrated under vacuum and dried to give 1.2 kg (83%) of camphor sulfonamide. In one experiment at 145 g scale of camphor sulfonic acid, the use of dichloromethane instead of chloroform for the reaction and extraction gives comparable yields.

To a suspension of the camphor sulfonamide (1.2 kg, 5.2 mol) in toluene (15 L) is added Amberlyst H+ resin (150 g), and the mixture is heated at reflux for 4 h with the water formed removed azeotropically using a Dean-Stark water separator. The reaction mixture is filtered hot to remove the resin. The filtrate on cooling gave a white solid which is collected by filtration to give 1.02 kg (92%) of the desired imine.

To the above imine (100 g, 0.47 mol) in ethanol (0.75 L) is added Raney Nickel (100 g) and the mixture is hydrogenated at 40 psi for 2 h. The catalyst is removed by filtration and the filtrate concentrated under vacuum to give the product 3-1 as a white solid; mp 182–186° C.; $^1$H NMR (CDCl$_3$): δ 0.94 (s, 3H), 1.13 (s, 3H), 1.32 (m, 1H), 1.46 (m, 1H), 1.82–2.04 (m, 5H), 3.12 (m, 2H), 3.43 (m, 1H), 4.10 (bs, 1H); $^{13}$C NMR (CDCl$_3$): δ 20.41, 26.72, 31.78, 35.98, 44.63, 47.38, 50.29, 54.90, 62.75. $[\alpha]^{25}_D$+32.07° (c=2.37, chloroform), Aldrich catalog $[\alpha]^{20}_D$+32° (c=5, chloroform). The total quantity of product obtained in 10 batches is 0.98 kg (97%) from 1 kg of the imine.

EXAMPLE 2

N-(Benzyl)-N-(methoxymethyl)-N-(trimethylsilylmethyl)amine (Scheme 3, 3-4)

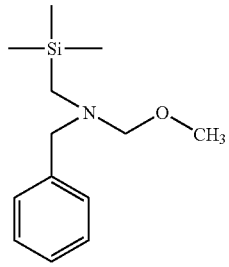

To a solution of chloromethyltrimethylsilane (1.34 kg, 10.96 mol) in acetonitrile (17.0 L) is added benzylamine (2.34 kg, 21.92 mol) and the reaction mixture is heated at reflux for 16 h. The reaction mixture is cooled to room temperature and the precipitate of benzylamine hydrochloride is removed by filtration. The filtrate is concentrated under vacuum to about 5 L and then diluted with water (5 L). The reaction mixture is extracted with hexane (2×5 L). The organic extracts are combined and washed with brine (5 L) and dried over MgSO$_4$. The filtrate is concentrated under vacuum to give 1.77 kg (83%) of N-(trimethylsilylmethyl)benzylamine.

The above amine (1.77 kg, 9.14 mol) is added to a mixture of 37% formaldehyde (0.89 kg, 10.96 mol) and methanol (0.35 kg, 10.96 mol) at 0° C. over a period of 30 min. The reaction mixture is further stirred at 0° C. for 1 h and at 10° C. to 15° C. for 3 h. To the reaction mixture is then added anhydrous K$_2$CO$_3$ (1 kg) and stirred for 2 h. The oily layer is decanted onto 100 g of K$_2$CO$_3$ and stirred for 15 min and again decanted. The remaining residual material from the K$_2$CO$_3$ is recovered by washing all the solid K$_2$CO$_3$ with ether. Ether washings are mixed with the decanted oily product and concentrated on rotary evaporator to give 2.10 kg (82%) of the desired product 3-4, deemed pure enough to be used in the next step.

EXAMPLE 3

(E)-3-Benzyloxypropenoyl-(2'S)-bornane-10,2-sultam (Scheme 3, 3-3)

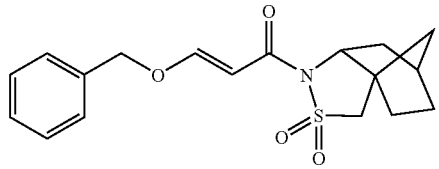

To a solution of (E)-3-benzyloxyacrylic acid (1.74 kg, 9.88 mol) and dichloromethane (20 L) is added thionyl chloride (1.75 kg, 14.7 mol) over a period of 30 min. The reaction mixture is heated at reflux and the SO$_2$ and HCl generated are scrubbed through a solution of aqueous NaOH. After 4 h (reaction progress is monitored by $^1$H NMR analysis), the solvent is removed under vacuum and the residual thionyl chloride is removed under vacuum overnight to give 2.00 kg (104%) of the desired acid chloride 3-2.

To a solution of camphor sultam (1.72 kg, 7.98 mol) in THF (16 L) at −40° C. is added methyl magnesium bromide (2.79 L, 8.38 mol; 3M solution in ether) at a dropwise rate while maintaining the internal temperature between −30° C. and −40° C. The reaction mixture is stirred for an additional hour at −40° C. To the anion at −40° C. is added slowly, acid chloride 3-2 (1.92 kg, 96% purity based upon the use of acid, 9.4 mol) in THF (8 L) while maintaining the internal temperature below −25° C. The reaction mixture is further stirred between −30° C. and −40° C. for 1 h and allowed to warm to +10° C. over a period of 5-6 h. The reaction mixture is then quenched with saturated aqueous NH$_4$Cl (16 L). The aqueous layer is separated and extracted twice with ethyl acetate (10 L). The combined organic layers are washed with saturated aqueous sodium carbonate (20 L) and brine (20 L). The organic layer is filtered through a pad of anhydrous MgSO$_4$ and concentrated under vacuum to dryness to furnish 3.12 kg of the crude product 3-3.

The crude product is taken up in ethyl acetate (8.3 L) and heated to 60° C. to dissolve the crude residue. The homogenous solution is diluted slowly with hexanes (30 L) while maintaining the solution at reflux. The reaction mixture is kept in a cold room for 16 h at 4° C. The crystalline material that separated is collected by filtration and washed with hexanes to give 1.906 kg (60%) of the desired product 3-3. The filtrate also contains the product, but no attempts are made to recover this material from the filtrate. $^1$H NMR (DMSO-d$_6$): δ 0.97 (s, 3H), 1.17 (s, 3H), 1.40 (m, 2H), 1.89 (m, 3H), 2.10 (m, 2H), 3.47 (d, J=6.0 Hz, 2H), 3.92 (dd, J=5.0 and 7.5 Hz, 1H), 4.95 (s, 2H), 6.05 (d, J=12.0 Hz, 1H), 7.37 (m, 5H), 7.78 (d, J=12.0 Hz, 1H); $^{13}$C NMR (DMSO-d$_6$): δ 19.92, 20.78, 26.56, 32.78, 38.55, 44.68, 47.81, 48.31, 53.08, 65.07, 73.25, 97.64, 99.61, 127.98, 128.64, 128.71, 134.92, 163.04, 164.77; IR (KBr) 2964, 2885, 1673, 1319, 1132 cm$^{-1}$; MS (ES$^+$) 376.34 (M+H)$^+$. $[\alpha]^{25}_D$+71.15 (c=0.52, chloroform); Anal. Calcd. for C$_{20}$H$_{25}$NO$_4$S: C, 63.97; H, 6.71; N, 3.73; S, 8.54. Found: C, 63.68; H, 6.78; N, 3.87; S, 8.66.

EXAMPLE 4

N-[[3S,4R)-4-Benzyloxy-1-(benzyl)pyrrolidin-3-yl]carbonyl]-(2'S)-bornane-10, 2-sultam (Scheme 3, 3-5)

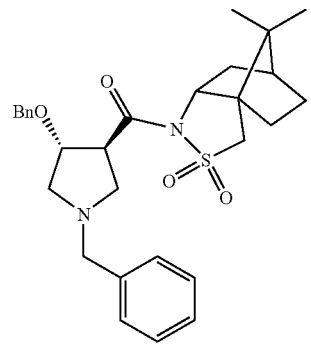

To a solution of 3-3 (1.83 kg, 4.88 mol) in dichloromethane (29 L) and trifluoroacetic acid (42 mL) is added 3-4 (2.32 kg, 9.76 mol) over a period of 30 min at room temperature. The reaction mixture is stirred for 15 min (reaction monitored for disappearance of starting materiel by NMR analysis of an aliquot). The reaction mixture is washed with 10% aqueous Na$_2$CO$_3$ (20 L) and brine (16 L). The reaction mixture is filtered through a pad of MgSO$_4$ and the filtrate is concentrated under vacuum. To the oily residue is added hexanes (10 L), and the mixture is stirred at room temperature overnight. The resulting solids are collected by filtration and washed with hexanes (4 L) then air dried for 3 h to furnish 2.26 kg product (NMR analysis shows the desired isomer comprises 91% of the mixture). Ethyl acetate (4.5 L) is added and the mixture is heated at reflux to dissolve the product. Hexanes are added while maintaining reflux (13.5 L, added at 1-L increment each). The mixture is then allowed to cool to room temperature with stirring for 16 h. The resulting solid obtained is collected by filtration and washed with 10% ethyl acetate in hexanes (5 L) affording 1.67 kg of the desired isomer as a white solid (NMR analysis showed a trace of the minor isomer). The solid is again subjected to recrystallization from ethyl acetate and hexanes as described above, the purified product collected by filtration, washed with 10% ethyl acetate in hexanes, and dried to furnish 1.46 kg (57.5%) of the desired isomer 3-5 as a white solid, mp 108–109° C. $^1$H NMR (CDCl$_3$): δ 0.94 (s, 3H), 1.02 (s, 3H), 1.37 (m, 2H), 1.88 (m, 3H), 2.04 (m, 2H), 2.57 (dd, J=9.5 and 5.6 Hz, 1H), 2.69 (dd, J=9.7 and 4.0 Hz, 1H), 2.92 (dd, J=9.7 and 6.5 Hz, 1H), 3.20 (t, J=9.0 Hz, 1H), 3.46 (m, 2H), 3.52 (m, 1H), 3.73 (m, 1H), 3.91 (t, J=6.0 Hz, 1H), 4.36 (d, J=11.5 Hz, 1H), 4.54 (d, J=11.5 Hz, 1H), 4.64 (m, 1H), 7.30 (m, 10H); $^{13}$C NMR (CDCl$_3$): δ 14.07, 19.72, 20.57, 20.92, 26.33, 32.61, 38.19, 44.04, 47.62, 48.29, 51.09, 52.89, 57.73, 59.28, 59.76, 60.26, 64.99, 71.25, 79.07, 99.45, 126.82, 127.40, 127.76, 128.07, 128.16, 128.53, 137.91, 138.32, 172.10; IR (KBr) 2776, 1698, 1311, 1215 cm$^{-1}$; MS (ES$^+$) 509.36 (M+H)$^+$. $[\alpha]^{25}_D$+86.9 (c=0.86, chloroform). Anal. Calcd for: $C_{29}H_{36}N_2O_4S$: C, 68.47; H, 7.13; N, 5.51; S, 6.30. Found: C, 68.58; H, 7.25; N, 5.51; S, 6.22.

For the minor isomer 3-6, $^1$H NMR (CDCl$_3$): δ 0.79 (s, 3H), 1.01 (s, 3H), 1.17 (m, 2H), 1.70 (m, 3H), 1.87 (m, 2H), 2.40 (dd, J=9.5 and 7.4 Hz, 1H), 2.57 (dd, J=10.0 and 6.2 Hz, 1H), 2.69 (dd, J=10.0 and 3.2 Hz, 1H), 3.10 (t, J=9.0 Hz, 1H), 3.25 (d, J=13.9 Hz, 1H), 3.34 (d, J=5.3 Hz, 1H), 3.39 (d, J=4.5 Hz, 1H), 3.52 (d, J=13.0 Hz, 1H), 3.62 (m, 1H), 3.70 (t, J=6.2 Hz, 1H), 4.17 (m, 2H), 4.38 (d, J=11.5 Hz, 1H), 7.10 (m, 10H); $^{13}$C NMR (CDCl$_3$): δ 14.61, 20.25, 21.37, 26.80, 33.33, 39.02, 45.16, 48.17, 48.75, 51.68, 53.58, 58.05, 60.15, 60.28, 60.79, 65.73, 71.62, 83.40, 127.37, 128.01, 128.19, 128.53, 128.63, 128.73, 129.21, 138.26, 138.84, 173.88; MS (ES$^+$) 509.36 (M+H)$^+$. $[\alpha]^{25}_D$+29.6 (c=1, ethanol).

EXAMPLE 5

(3R,4R)-(1-Benzyl-4-benzyloxypyrrolidin-3-yl) methanol (Scheme 3, 3-7)

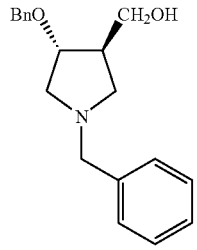

To a stirred mixture of lithium aluminum hydride (344 g, 8.6 mole) in THF (8.6 L) under a nitrogen atmosphere is added dropwise, compound 3–5 (1.46 kg, 2.87 mole) in THF (3.5 L) at 0° C. over a period of 2 h. The reaction mixture is stirred at 0° C. for 1 h and allowed to warm to room temperature over a period of 2.5 h (TLC analysis showed complete reduction). The reaction mixture is cooled to 0° C. and quenched by careful addition of water (750 mL) and diluted with ethyl acetate (15 L). The solid cake is filtered through Celite® and the cake washed with ethyl acetate (4×2.5 L). The filtrate is extracted with 2 N HCl (6×3 L). The organic layer is discarded, the aqueous layer is cooled to 0° C., and the pH is adjusted to 13 using solid NaOH (3.64 kg). The basified aqueous layer is extracted with ethyl acetate (3×8 L). The organic layers are combined, washed with brine (4 L), filtered through a pad of MgSO$_4$, and the filtrate concentrated under vacuum to dryness giving 756 g of the desired product 3–7 (89%) as a colorless oil that solidified on standing, mp 62–64° C.

$^1$H NMR (CDCl$_3$): δ 2.31 (m, 1H), 2.42 (dd, J=4.5 and 10.0 Hz, 1H), 2.62 (dd, J=9.2 and 3.0 Hz, 1H), 2.74 (dd, J=9.0 and 7.0 Hz, 1H), 3.11 (dd, J=9.8 and 6.5 Hz, 1H), 3.45 (bs, 1H), 3.61 (m, 3H), 3.67 (dd, J=10.0 and 4.5 Hz, 1H), 4.03 (m, 1H), 4.46 (s, 2H), 7.30 (m, 10H); $^{13}$C NMR (CDCl$_3$): δ 26.44, 46.97, 47.22, 57.26, 60.90, 61.25, 66.65, 72.17, 74.42, 82.10, 128.04, 128.50, 128.54, 129.01, 129.21, 129.25, 129.55, 139.03, 139.09; IR (KBr) 3224, 3030, 1456, 1351, 1143, 1094 cm$^{-1}$; MS (ES$^+$) 298.46 (M+H)$^+$. $[\alpha]^{25}_D$+16.7 (c=0.52, chloroform). Anal. Calcd for: $C_{19}H_{23}NO_2$: C, 76.73; H, 7.80; N, 4.71; Found: C, 76.84; H, 7.95; N, 4.76.

EXAMPLE 6

(3R,4R)-4-(Hydroxymethyl)pyrrolidin-3-ol Hydrochloride (Scheme 3, Ia)

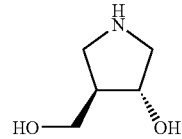

To a solution of 3–7 (70 g, 0.235 mol) in ethanol (700 mL) is added a 4-M solution of HCl in dioxane (59 mL, 0.235 mol) and palladium on carbon (10%, 50 g). The resulting slurry is hydrogenated at 70 psi for 2 days. The catalyst is removed by filtration through Celite® and concentrated under vacuum and dried to furnish 38 g (100%) of Ia, homogeneous by TLC analysis (75% CMA-50 in CMA-80). $^1$H NMR (DMSO-d$_6$): δ 2.21 (m, 1H), 2.96 (dd, J=5.0 and 12.0 Hz, 1H), 3.19 (dd, J=12.0 and 5.0 Hz, 1H), 3.29 (dd, J=7.7 and 3.8 Hz, 1H), 3.38 (m, 3H), 4.15 (m, 1H), 4.94 (t, J=5.0 Hz, 1H), 5.44 (d, J=3.8 Hz, 1H), 9.15 (bs, 2H); $^1$H NMR (D$_2$O): δ 4.44-4.40 (m, 1H), 3.67-3.57 (m, 3H), 3.43 (dd, J=5.1 and 12.6 Hz, 1H), 3.27 (dd, J=12.6 and 2.5 Hz, 1H), 3.16 (dd, J=5.7 and 12.3 Hz, 1H), 2.5314 2.43 (m, 1H); $^{13}$C NMR (D$_2$O): 46.54, 47.86, 52.07, 60.83, 71.82; IR (KBr) 3835, 2955, 1616, 1396, 1050 cm$^{-1}$; MS (ES$^+$) 118.71 (100%; M$^{+1}$). $^1$HNMR and $^{13}$C NMR data are consistent with the literature reports. An analytical sample is prepared by purifying 0.5 g on a silica gel column (10 g), eluting with CMA-80/CMA-50 to furnish product as an oil. The product obtained is dissolved in methanol (5 mL) and 1 mL conc. HCl is added. This is stirred at room temperature for 5 min and concentrated under vacuum to dryness to furnish desired product 1 as hydrochloride salt. Anal. Calcd for $C_5H_{11}NO_2$·HCl·0.5 H$_2$O; C, 36.92; H, 8.06; N, 8.68. Found: C, 37.32; H, 8.00; N, 8.52. $[\alpha]^{25}_D$+17.53 (c=1.175, methanol).

EXAMPLE 7

(2S,3R)-Diethyl 2-(benzyloxymethoxy)-3-(benzyloxymethyl)succinate (Scheme 4, 4-2)

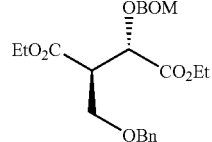

To a solution of diisopropylamine (9.05 mL, 64.6 mmol) in THF (100 mL) is added dropwise n-BuLi (1.6 M in hexanes, 36.5 mL, 58.3 mmol) at 0° C. over a period of 10 min under nitrogen atmosphere. The LDA formed is stirred further at 0° C. for 30 min and cooled to −78° C. and to this is added dropwise (S)-diethyl malate (5.04 g, 26.5 mmol, $[\square\square]^{25}_D$−15.53° (c 12.08, acetone) over a period of 10 min. The reaction mixture is further stirred at −78° C. for 30 min and warmed to −20° C. and maintained at −20° C. for 1 h. After cooling to −78° C. again, BOM-Cl (11 mL, 79.5 mmol) is added over a period of 10 min and is stirred at this temperature for 6 h and at room temperature for 24 h. The reaction mixture is quenched with glacial acetic acid (7.5 mL) in ether (10 mL) and poured into 100 mL water. The mixture is extracted with ether (4×100 mL) and the combined organic layers are washed with brine (100 mL), dried (MgSO$_4$), filtered and concentrated to furnish an oily residue. Purification of the crude product by flash column chromatography (300 g, silica gel) eluting with ethyl acetate in hexanes (0% to 30%) furnishes 7.92 g (69%) of 4-2 as an oil; $^1$H NMR (DMSO-d$_6$): δ 7.37–7.23 (m, 10H), 4.76 (s, 2H), 4.54 (s, 2H), 4.46–4.45 (m, 3H), 4.13–4.01 (m, 4H), 3.74–3.58 (m, 2H), 3.17 (dd, J=7 and 12 Hz, 1H), 1.16 (t, J=7 Hz, 3H), 1.15 (t, J=7 Hz, 3H); IR (KBr) 3019, 2901, 1735, 1455, 1374, 1215, 1040, cm$^{-1}$; MS (ES$^+$) 453.39 [100% (M+Na)$^+$]; Anal. (C$_{24}$H$_{30}$O$_7$) C, H. [α]$^{25}_D$ –38.15° (c 1.28, acetone).

EXAMPLE 8

(2S,3R)-2-(Benzyloxymethoxy)-3-(benzyloxymethyl)butane-1,4-diol (Scheme 4, 4-3)

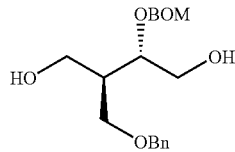

A solution of 4-2 (9 g, 21.12 mmol) in THF (20 mL) is added to a mixture of LAH (1.61 g, 42.23 mmol) in THF (20 mL) at 0° C. over a period of 30 min. The reaction mixture is heated at reflux for 4 h and quenched by dropwise addition of water (3 mL) after cooling to 0° C. The reaction mixture is filtered through a pad of Celite and MgSO$_4$ and the cake washed with 1000 mL ethyl acetate. The filtrate is concentrated under vacuum and the residue purified by flash column chromatography (275 g silica gel, eluting with 0 to 25% chloroform:methanol:ammonium hydroxide [80:18:2] in chloroform) to furnish 5.56 g (76%) of 4-3 as an oil: $^1$H NMR (CDCl$_3$): δ 7.41-7.29 (m, 10H), 4.89 (d, J=7.0 Hz, 1H), 4.77 (d, J=7.0 Hz, 1H), 4.72-4.59 (dd, J=12.0 and 25.0 Hz, 2H), 4.50 (s, 2H), 3.92-3.85(m, 1H), 3.81-3.78 (d, J=4.5 Hz, 2H), 3.75 (bs, 1H), 3.67 (d, J=5.0 Hz, 1H), 3.62 (d, J=6.0 Hz, 2H), 3.16 (bs, 1H), 2.76 (bs, 1H), 2.12-2.03 (m, 1H); IR (KBr): 3432, 3014, 2886, 1454, 1365, 1216, 1026 cm$^{-1}$; MS (ES$^+$) 369.41 [(M+Na)+]. Anal. (C$_{20}$H$_{26}$O$_5$.0.25H$_2$O)C, H. [□□$^{25}_D$–7.5° (c 1.45, acetone).

EXAMPLE 9

(2S,3S)-2-(Benzyloxymethoxy)-3-(benzyloxymethyl)butane-1,4-diyl dimethanesulfonate (Scheme 4, 4-4)

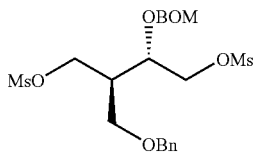

Compound 4-3 (10.5 g, 30.3 mmol) is added to a solution of methane sulfonyl chloride (7 mL, 90.9 mmol) in pyridine (30 mL) at 0° C. over a period of 1 h and allowed to warm to room temperature overnight. The reaction mixture is concentrated under vacuum and to the residue is added 0.5 N aqueous HCl (100 mL) and ether (100 mL). The organic layer is separated and washed with brine (50 mL), dried (MgSO$_4$), filtered and concentrated. The residue is purified by flash column chromatography (400 g silica gel, eluting with 0–50% ethyl acetate in hexanes) to furnish 9.45 g (62%) of 4-4 as an oil: $^1$H NMR (DMSO-d$_6$): δ 7.36–7.28 (m, 10H), 4.82 (q, J=7.0 Hz, 2H), 4.59 (dd, J=12.0 and 16.0 Hz, 2H), 4.47 (s, 2H), 4.45–4.37 (m, 2H), 4.31–4.24 (m, 2H), 4.02 (m, 1H), 3.55 (d, J=5.0 Hz, 2H), 3.16 (s, 6H), 2.14–2.31 (m, 1H); IR (KBr): 3546, 3026, 2940, 2881, 1734, 1455, 1360 cm$^{-1}$; MS (ES$^+$) 525.31 [(M+Na)$^+$]. Anal. (C$_{22}$H$_{30}$O$_9$S$_2$) C, H. [α]$^{25}_D$ –4.37° (c 1.15, ethanol).

EXAMPLE 10

(3S,4R)-1-Benzyl-3-(benzyloxymethoxy)-4-(benzyloxymethyl)pyrrolidine (Scheme 4, 4-5)

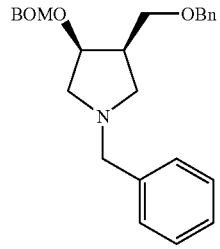

A mixture of 4-4 (8.78 g, 17.5 mmol) and benzylamine (90 mL) is heated at 60° C. for 16 h. The reaction mixture is concentrated to remove most of benzyl amine and to the residue added ethyl acetate (100 mL) and hexanes (100 mL). The mixture is filtered to remove solids and the filtrate concentrated. The residue is purified by flash column chromatography (250 g, silica gel, eluting with 0-50% ethyl acetate in hexanes) to furnish 6.41 g (88%) of 4-5 as an oil: $^1$H NMR (CDCl$_3$): δ 7.24-7.26 (m, 15H), 4.73 (q, J=7.0 Hz, 2H), 4.54 (dd, J =12.0 and 17.0 Hz, 2H), 4.50 (s, 2H), 4.34 (m, 1H), 3.75-3.58 (m, 3H), 3.50 (dd, J=7.5 and 9.0 Hz, 1H), 2.99 (dd, J=5.5 and 10.0 Hz, 1H), 2.86 (dd, J=7.0 and 8.0 Hz, 1H), 2.58 (m, 2H), 2.46 (t, J=9.0 Hz, 1H); IR (KBr): 3013, 2942, 2864, 2797, 1495, 1454 cm$^{-1}$; MS (ES$^+$) 418.41 [M+1]. Anal. (C$_{27}$H$_{31}$NO$_3$) C, H, N. [α]$^{25}_D$ –8.60 (c 1.17, ethanol).

EXAMPLE 11

(3S,4R)-4-(Hydroxymethyl)pyrrolidin-3-ol as hydrochloride (Scheme 4, Ib)

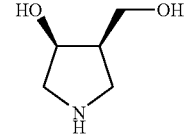

To a mixture of 4–5 (1.04 g, 2.5 mmol) and Pd/C (10%, 1 g) in ethanol (25 mL) is added conc. HCl (0.41 mL, 5 mmol) and hydrogenated at 70 psi for 4 days. The reaction mixture is filtered through Celite to remove catalyst and concentrated under vacuum to dryness to furnish 0.38 g (100%) of Ib as a semisolid. An analytical sample is prepared by crystallization from ethanol/ether to furnish Ib as a white solid: mp 94–96° C.; $^1$H NMR (DMSO-d$_6$): δ 9.21 (bs, 2H, NH$_2$$^+$), 5.39 (d, J=4.0 Hz, 1H, 3-OH), 4.72 (t, J=5.0 Hz, 1H, 6-OH), 4.26 (dd, J=7.5 and 3.5 Hz, 1H, H-3), 3.65–3.55 (m, 1H, H-6), 3.48-3.38 (m, 1H, H-6), 3.29-3.12 (m, 2H, H-2α, H-5α), 3.04 (d, J=12.0 Hz, 1H, H-2α, 2.84 (t, J=11.0 Hz, 1H, H-5β), 2.29-2.12 (m, 1H, H-4); $^{13}$CNMR (DMSO-d$_6$): δ 45.59, 46.35, 53.02, 58.33, 69.03; IR (KBr) 3370, 3012, 2921, 1590, 1398, 1317 cm$^{-1}$; MS (ES$^+$) 118.72 [M+1]. Anal. (C$_5$H$_{11}$NO$_2$.HCl) C, H, N. [α]$^{25}_D$–19.8° (c=0.61, methanol).

What is claimed is:

1. A process for the preparation of compound (Ia) where R and $R_1$ are trans to each other in formula (1)

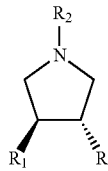
(Ia)

wherein
R is selected from the group consisting of H, $OR_2$, $N_3$, $NHR_2$ and F;
$R_1$ is selected from the group consisting of $CH_3$, $CH_2OR_2$, $CH_2N_3$, $CH_2NHR_2$, $CH_2F$, CHO, $CH=NR_2$, $CO_2H$, $CO_2$ alkyl, $CONHR_2$, $CH_2CH_2OR_2$, $CH=CHCO_2R_3$, $CH_2CH_2CO_2R_3$ and $CH_2CH_2CH_2OR_2$;
$R_2$ is selected from the group consisting of H, $R_3$, $CH_2R_3$, $C(O)R_3$ and $C(O)OR_3$; and
$R_3$ is selected from the group consisting of alkyl and aryl; and pharmaceutically acceptable salts thereof;
which comprises:
i) reacting camphor sulfonic acid with thionyl chloride; further contacting the resultant camphor sulfonyl chloride with ammonia to generate camphor sulfonamide; and eliminating water from the amide under acidic conditions to produce an imine; and hydrogenating the resultant imine with hydrogen in the presence of a suitable catalyst to produce camphor sultam;
ii) further reacting (E)-3-benzyloxyacrylic acid chloride with camphor sultam and a base to yield the addition product (E)-3-benzyloxypropenoyl-(2'S)-borane-10,2-sultam
iii) contacting chloromethyltrimethylsilane with benzylamine to generate N-(trimethylsilylmethyl)benzylamine and further reacting N-(trimethylsilylmethyl) benzylamine with formaldehyde and methanol to produce N-(benzyl)-N-(methoxymethyl)-N-(trimethylsilylmethyl)amine;
iv) reacting compound (E)-3-benzyloxypropenoyl-(2'S)-borane-10,2-sultam with N-(benzyl)-N-(methoxymethyl)-N-(trimethylsilylmethyl)amine in the presence of a acid catalyst to produce pyrrolidine derivatives N-[[3S,4R)-4-Benzyloxy-1-(benzyl)pyrrolidin-3-yl]carbonyl]-(2'S)-bornane-10,2-sultam and N-[[3R,4S)-4-Benzyloxy-1-(benzyl)pyrrolidin-3-yl]carbonyl]-(2'S)-bornane-10,2-sultam as a mixture of isomers and isolating the desired isomer N-[[3S,4R)-4-Benzyloxy-1-(benzyl)pyrrolidin-3-yl]carbonyl]-(2'S)-bornane-10,2-sultam;
v) reducing compound N-[[3S,4R)-4-Benzyloxy-1-(benzyl)pyrrolidin-3-yl]carbonyl]-(2'S)-bornane-10,2-sultam with a reducing agent, and isolating the pyrrolidine derivative (3R,4R)-(1-Benzyl-4-benzyloxypyrrolidin-3-yl)methanol;
vi) deprotecting the (3R,4R)-(1-Benzyl-4-benzyloxypyrrolidin-3-yl)methanol through hydrogenation in the presence of a catalyst to produce the desired compound of formula (Ia).

2. The process of claim 1 wherein the base comprises methyl magnesium bromide.

3. The process of claim 1 wherein the acid catalyst comprises trifluoroacetic acid.

4. The process of claim 1 wherein the reducing agent comprises lithium aluminum hydride.

5. The process of claim 1 wherein the hydrogenation catalyst comprises Pd/C.

6. A process for the preparation of compound (Ia), where R=OH, $R_1$=$CH_2OH$ and $R_2$=H and R and $R_1$ are trans to each other in formula (I)

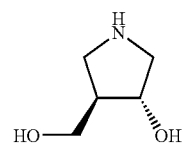
(Ia)

which comprises:
i) reacting camphor sulfonic acid with thionyl chloride; further contacting the resultant camphor sulfonyl chloride with ammonia to generate camphor sulfonamide; eliminating water from the amide under acidic conditions to produce an imine; and hydrogenating the resultant imine with hydrogen to produce camphor sultam;
ii) further reacting (E)-3-benzyloxyacrylic acid chloride with camphor sultam and a base to yield the addition product (E)-3-benzyloxypropenoyl-(2'S)-borane-10,2-sultam;
iii) contacting chloromethyltrimethylsilane with benzylamine to generate N-(trimethylsilylmethyl)benzylamine and further reacting N-(trimethylsilylmethyl) benzylamine with formaldehyde and methanol to produce N-(benzyl)-N-(methoxymethyl)-N-(trimethylsilylmethyl)amine;
iv) reacting compound (E)-3-benzyloxypropenoyl-(2'S)-borane-10,2-sultam with N-(benzyl)-N-(methoxymethyl)-N-(trimethylsilylmethyl)amine in the presence of a acid catalyst to produce pyrrolidine derivatives N-[[3S,4R)-4-Benzyloxy-1-(benzyl)pyrrolidin-3-yl]carbonyl]-(2'S)-bornane-10,2-sultam and N-[[3R,4S)-4-Benzyloxy-1-(benzyl)pyrrolidin-3-yl]carbonyl]-(2'S)-bornane-10,2-sultam as a mixture of isomers and isolating the desired isomer N-[[3S,4R)-4-Benzyloxy-1-(benzyl)pyrrolidin-3-yl]carbonyl]-(2'S)-bornane-10,2-sultam;
v) reducing compound N-[[3S,4R)-4-Benzyloxy-1-(benzyl)pyrrolidin-3-yl]carbonyl]-(2'S)-bornane-10,2-sultam with a reducing agent and isolating the pyrrolidine derivative (3R,4R)-(1-Benzyl-4-benzyloxypyrrolidin-3-yl)methanol;
vi) deprotecting compound (3R,4R)-(1-Benzyl-4-benzyloxypyrrolidin-3-yl)methanol through hydrogenation in the presence of a catalyst to produce the desired compound of formula (Ia).

7. The process of claim 6 wherein the base comprises methyl magnesium bromide.

8. The process of claim 6 wherein the acid catalyst comprises trifluoroacetic acid.

9. The process of claim 6 wherein the reducing agent comprises lithium aluminum hydride.

10. The process of claim 6 wherein the hydrogenation catalyst comprises Pd/C.

* * * * *